(12) United States Patent
Shintani

(10) Patent No.: US 11,511,160 B2
(45) Date of Patent: Nov. 29, 2022

(54) BALANCE TRAINING SYSTEM, METHOD OF CONTROLLING THE SAME, AND CONTROL PROGRAM

(71) Applicant: TOYOTA JIDOSHA KABUSHIKI KAISHA, Toyota (JP)

(72) Inventor: Kazuhiro Shintani, Toyokawa (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 227 days.

(21) Appl. No.: 17/122,032

(22) Filed: Dec. 15, 2020

(65) Prior Publication Data
US 2021/0245009 A1    Aug. 12, 2021

(30) Foreign Application Priority Data

Feb. 12, 2020   (JP) .............................. JP2020-021522

(51) Int. Cl.
*A63B 26/00*   (2006.01)
*A63B 24/00*   (2006.01)
(Continued)

(52) U.S. Cl.
CPC ............ *A63B 26/003* (2013.01); *A63B 22/02* (2013.01); *A63B 24/0062* (2013.01);
(Continued)

(58) Field of Classification Search
CPC .............. A61B 5/4023; A63B 2225/50; A63B 2220/833; A63B 2220/52; A63B 2220/50; A63B 2208/0204; A63B 2071/025; A63B 2022/0094; A63B 71/06; A63B 24/0062; A63B 24/0075; A63B 24/0087; A63B 22/02; A63B 26/003
(Continued)

(56) References Cited

U.S. PATENT DOCUMENTS 5,562,572 A * 10/1996 Carmein ................. A63B 22/02
                                                              198/779
6,152,854 A * 11/2000 Carmein ................. G06F 3/011
                                                              198/779
(Continued)

FOREIGN PATENT DOCUMENTS

| JP | 2015-100477 A | 6/2015 |
|---|---|---|
| JP | 6260811 B2 | 1/2018 |
| WO | 2018/016765 A1 | 1/2018 |

*Primary Examiner* — Sundhara M Ganesan
*Assistant Examiner* — Thao N Do
(74) *Attorney, Agent, or Firm* — Oliff PLC

(57) ABSTRACT

A balance training system including a riding plate; a load distribution sensor; a load sensor; a mobile body on which the riding plate, the load distribution sensor, and the load sensor are disposed; and a control unit configured to calculate a reference position based on positions of feet of a trainee detected by the load distribution sensor, then calculate a center of gravity position of the trainee based on the load detected by the load sensor, and control a movement of the mobile body based on a change of the center of gravity position with respect to the reference position. The control unit is configured to update the reference position based on the changed positions of the feet of the trainee when the change of the position of at least one of the feet of the trainee is detected by the load distribution sensor.

6 Claims, 6 Drawing Sheets

(51) Int. Cl.
*A63B 22/02* (2006.01)
*A63B 22/00* (2006.01)
*A63B 71/06* (2006.01)
*A63B 71/02* (2006.01)
*A61B 5/00* (2006.01)

(52) U.S. Cl.
CPC ...... *A63B 24/0075* (2013.01); *A63B 24/0087* (2013.01); *A61B 5/4023* (2013.01); *A63B 71/06* (2013.01); *A63B 2022/0094* (2013.01); *A63B 2071/025* (2013.01); *A63B 2208/0204* (2013.01); *A63B 2220/50* (2013.01); *A63B 2220/52* (2013.01); *A63B 2220/833* (2013.01); *A63B 2225/50* (2013.01)

(58) Field of Classification Search
USPC .......................................................... 482/4
See application file for complete search history.

(56) References Cited

U.S. PATENT DOCUMENTS

| | | | | |
|---|---|---|---|---|
| 7,780,573 | B1* | 8/2010 | Carmein | A63B 71/0622 482/4 |
| 8,315,822 | B2* | 11/2012 | Berme | G01L 5/16 702/41 |
| 8,480,541 | B1* | 7/2013 | Brunts | A63B 22/025 482/7 |
| 9,149,222 | B1* | 10/2015 | Zets | A61B 5/4023 |
| 9,814,920 | B1* | 11/2017 | Monterrey | A63B 21/0552 |
| 10,117,602 | B1* | 11/2018 | Berme | A61B 5/1128 |
| 10,376,734 | B1* | 8/2019 | Razon | A61B 5/0077 |
| 11,311,209 | B1* | 4/2022 | Berme | A61B 5/1038 |
| 11,376,471 | B2* | 7/2022 | Yamaguchi | A61H 1/00 |
| 11,395,941 | B2* | 7/2022 | Kikuchi | A63B 24/0062 |
| 2006/0217233 | A1* | 9/2006 | Lee | A63B 21/00047 482/9 |
| 2008/0228110 | A1* | 9/2008 | Berme | A63B 26/003 600/595 |
| 2010/0093492 | A1* | 4/2010 | Watterson | A63B 22/0242 482/4 |
| 2010/0160115 | A1* | 6/2010 | Morris | A63B 22/0235 482/4 |
| 2010/0304931 | A1* | 12/2010 | Stumpf | A63B 24/0021 340/8.1 |
| 2011/0021316 | A1* | 1/2011 | Saitou | A63B 22/203 482/52 |
| 2011/0312473 | A1* | 12/2011 | Chu | A63B 69/0053 482/54 |
| 2015/0343266 | A1* | 12/2015 | Vardy | A61B 5/1036 482/8 |
| 2016/0158622 | A1* | 6/2016 | Yamazaki | A63B 69/0064 482/7 |
| 2016/0228746 | A1* | 8/2016 | Jayakumar | G16H 40/63 |
| 2017/0136289 | A1* | 5/2017 | Frank | A63B 22/025 |
| 2017/0225038 | A1* | 8/2017 | Wei | A63B 22/0242 |
| 2017/0266483 | A1* | 9/2017 | Dalebout | A63B 71/0622 |
| 2017/0266534 | A1* | 9/2017 | Watterson | A63B 24/0087 |
| 2017/0326411 | A1* | 11/2017 | Watterson | A63B 22/0214 |
| 2018/0229074 | A1* | 8/2018 | Sasaki | A63B 24/0006 |
| 2018/0289579 | A1* | 10/2018 | Agrawal | A61B 5/112 |
| 2019/0030399 | A1* | 1/2019 | D'Alesio | A63B 21/00181 |
| 2019/0307387 | A1* | 10/2019 | An | A63B 26/003 |
| 2020/0289035 | A1* | 9/2020 | Sato | A63B 22/20 |

* cited by examiner

BALANCE TRAINING SYSTEM, METHOD OF CONTROLLING THE SAME, AND CONTROL PROGRAM

CROSS REFERENCE TO RELATED APPLICATIONS

This application is based upon and claims the benefit of priority from Japanese patent application No. 2020-021522, filed on Feb. 12, 2020, the disclosure of which is incorporated herein in its entirety by reference.

BACKGROUND

The present disclosure relates to a balance training system, a method of controlling the same, and a control program.

The rehabilitation support device disclosed in Japanese Patent No. 6260811 includes a force plate on which a subject can stand, a load detection sensor for detecting a load of the subject applied to the force plate, center of gravity position detection means for detecting a center of gravity position of the subject from the load detected by the load detection sensor, and driving means. Here, the driving means moves the force plate in accordance with the moving direction of the center of gravity of the subject.

SUMMARY

Usually, a rehabilitation support device moves a force plate in association with the movement of the center of gravity without a subject moving his/her feet from an initial standing position after the subject (trainee) gets on the force plate and decides the initial standing position on the force plate. This enables the subject to perform balance training.

However, in the related art, only the load of the subject is detected, not the standing position of the subject. Therefore, in the related art, when the standing position of the subject changes during the balance training, even if the position of the center of gravity (reference center of gravity position) in the stationary standing state changes along with the change of the standing position, the change of the standing position is not detected, and the reference center of gravity position is maintained at the first set position. That is, a deviation is generated between the actual reference center of gravity position and the theoretical reference center of gravity position. As a result, there has been a problem in the related art that the subject cannot perform effective balance training, because the movement of the force plate cannot be accurately controlled in association with the movement of the center of gravity of the subject.

The present disclosure has been made in view of the above circumstances. An object of the present disclosure is to provide a balance training system, a method of controlling the same, and a control program capable of performing effective training even when a standing position of a trainee changes.

An example aspect of the present disclosure is a balance training system including: a riding plate including a mounting surface for supporting a sole of a trainee in a standing state; a load distribution sensor including a plurality of sensors arranged in a matrix on the riding plate and configured to detect positions of feet of the trainee riding on the riding plate; a load sensor configured to detect a load received by the riding plate from the trainee; a mobile body, the riding plate, the load distribution sensor, and the load sensor being disposed on the mobile body; and a control unit configured to calculate a reference position based on the positions of the feet of the trainee detected by the load distribution sensor, then calculate a center of gravity position of the trainee based on the load detected by the load sensor, and control a movement of the mobile body based on a change of the center of gravity position with respect to the reference position. The control unit is configured to update the reference position based on the changed positions of the feet of the trainee when the change of the position of at least one of the feet of the trainee is detected by the load distribution sensor. In this balance training system, even when the standing position of the trainee is changed, the reference position is reset based on the changed standing position of the trainee. This enables control of the movement of the mobile body accurately according to the change of the center of gravity position with respect to the reset reference position, so that the trainee can perform effective balance training.

The control unit may be configured to control a moving direction and a moving amount of the mobile body based on a changing direction and a changing amount of the center of gravity position of the trainee with respect to the reference position.

Further, the mobile body is, for example, a belt of a treadmill, and the load distribution sensor is disposed, for example, on the belt of the treadmill.

Further, for example, the mobile body is a moving carriage, and the load distribution sensor is mounted on the moving carriage.

Another example aspect of the present disclosure is a method of controlling a balance training system including: detecting, using a load distribution sensor composed of a plurality of sensors arranged in a matrix on a riding plate, positions of feet of a trainee riding on the riding plate, the riding plate including a mounting surface for supporting a sole of the trainee in a standing state; detecting, using a load sensor, a load received by the riding plate from the trainee; and calculating a reference position based on the positions of the feet of the trainee detected by the load distribution sensor, then calculating a center of gravity position of the trainee based on the load detected by the load sensor, and controlling a movement of a mobile body, on which the riding plate, the load distribution sensor, and the load sensor are disposed, based on a change of the center of gravity position with respect to the reference position. In the controlling of the movement of the mobile body, the reference position is updated based on the changed positions of the feet of the trainee when the change of the position of at least one of the feet of the trainee is detected by the load distribution sensor. In this method of controlling the balance training system, even when the standing position of the trainee is changed, the reference position is reset based on the changed standing position of the trainee. This enables control of the movement of the mobile body accurately according to the change of the center of gravity position with respect to the reset reference position, so that the trainee can perform effective balance training.

Another example aspect of the present disclosure is a control program for causing a computer to execute: a process of detecting, using a load distribution sensor composed of a plurality of sensors arranged in a matrix on a riding plate, positions of feet of a trainee riding on the riding plate, the riding plate including a mounting surface for supporting a sole of the trainee in a standing state; a process of detecting, using a load sensor, a load received by the riding plate from the trainee; and a process of calculating a reference position based on the positions of the feet of the trainee detected by the load distribution sensor, then calculating a center of gravity position of the trainee based on the load detected by the load sensor, and controlling a movement of a mobile body, on which the riding plate, the load distribution sensor, and the load sensor are disposed, based on a change of the center of gravity position with respect to the reference position. In process of the controlling the movement of the mobile body, the reference position is updated based on the changed positions of the feet of the trainee when the change of the position of at least one of the feet of the trainee is detected by the load distribution sensor. In this control program, even when the standing position of the trainee is changed, the reference position is reset based on the changed standing position of the trainee. This enables control of the movement of the mobile body accurately according to the change of the center of gravity position with respect to the reset reference position, so that the trainee can perform effective balance training.

According to the present disclosure, it is possible to provide a balance training system, a method of controlling the same, and a control program capable of performing effective balance training even when a standing position of a trainee changes.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Hereinafter, the present disclosure will be explained through embodiments of the present disclosure. However, they are not intended to limit the scope of the present disclosure according to the claims. Further, all of the components/structures described in the embodiments are not necessarily indispensable as means for solving the problem. For clarifying the explanation, the following description and the drawings are partially omitted and simplified as appropriate. The same symbols are assigned to the same elements throughout the drawings and repeated explanations are omitted as appropriate.

First Embodiment

Figure 1:
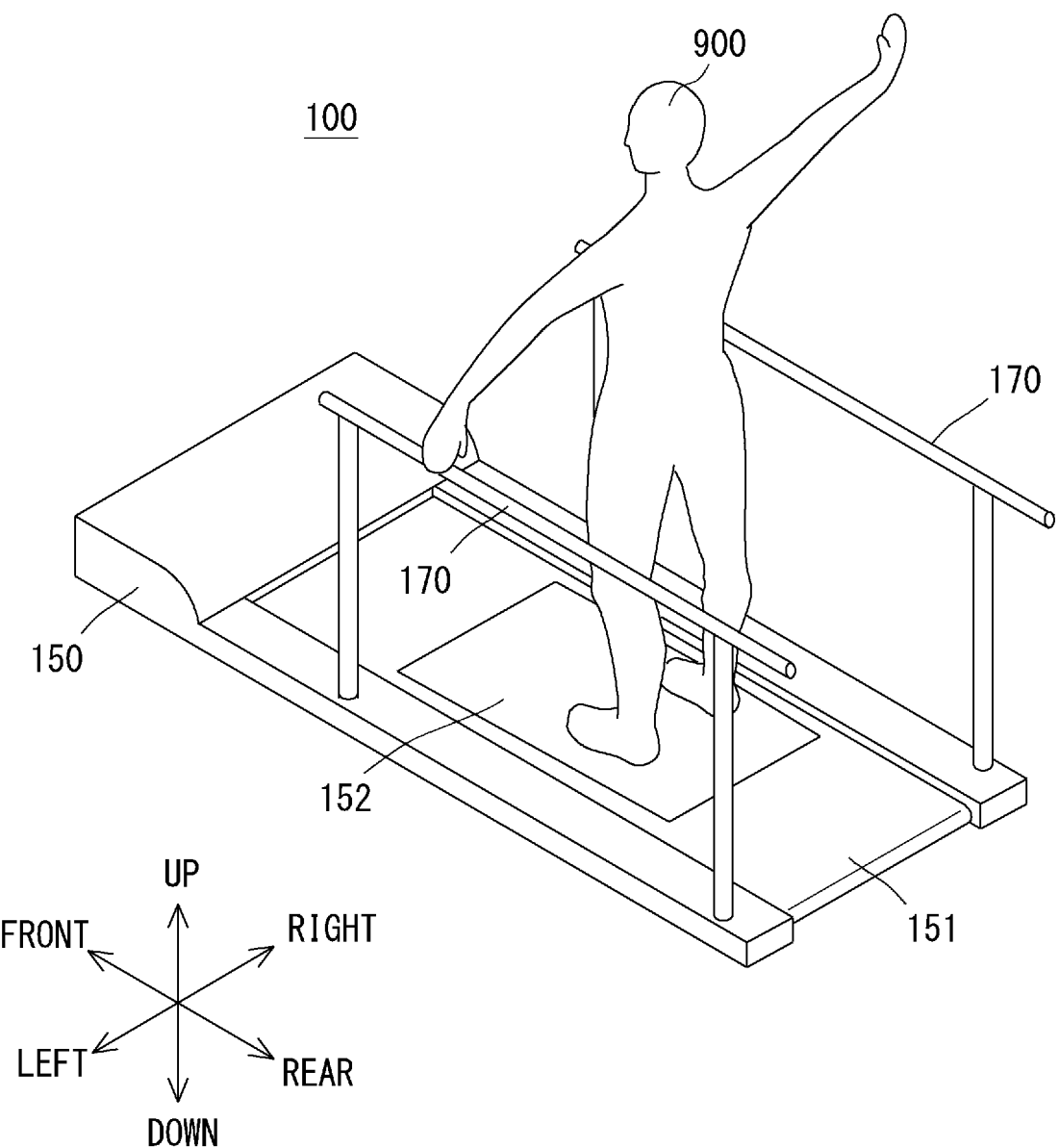
FIG. 1 is an overview perspective view of a balance training system according to a first embodiment.
Figure 2:
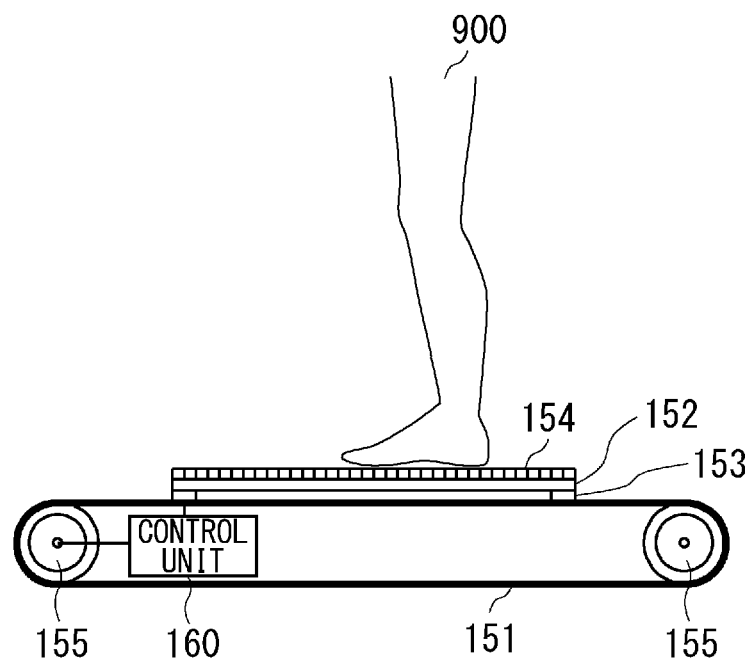
FIG. 2 is an overview side view of a part of the balance training system shown in FIG. 1.
Figure 2:
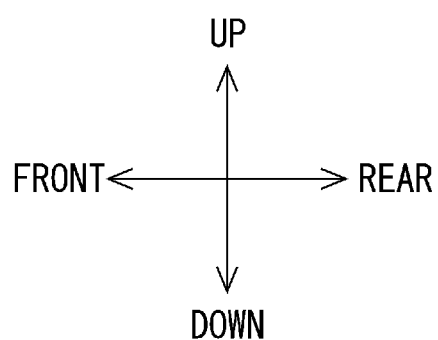

FIG. 1 is an overview perspective view (view from diagonally backward left) of a balance training system 100 according to a first embodiment. FIG. 2 is an overview side view (view from the left) of a part of the balance training system 100. The balance training system 100 may also be referred to as a balance training device.

The balance training system 100 is a system for a trainee with a disability such as hemiplegia to learn to move his/her center of gravity, which the learning of moving is necessary for walking, or for a trainee with a disability in his/her ankle joint to recover the ankle joint function. For example, when a trainee 900 who wants to recover the ankle joint function tries to continue to stay riding on the balance training system 100 while maintaining his/her balance, the balance training system 100 can apply a load that can be expected to have a rehabilitation effect to the trainee 900's ankle joint.

Specifically, the balance training system 100 includes a treadmill 150, a riding plate 152, load sensors 153, a load distribution sensor 154, a control unit 160, and a handrail 170. Note that, in the following description, the up-down direction, the right-left direction, and the front-rear direction are directions based on the orientation of the trainee 900.

The treadmill 150 includes at least a ring-shaped belt (mobile body) 151, a pulley 155, and a motor (not shown). The riding plate 152, the load sensors 153, and the load distribution sensor 154 are disposed on the belt 151.

The riding plate 152 is a riding part on which the trainee 900 rides, and has a mounting surface for supporting the sole of the trainee 900 in a standing state. As the riding plate 152, a rectangular flat plate made of, for example, polycarbonate resin, which has relatively high rigidity to withstand the riding of the trainee 900, is used. The riding plate 152 is supported on an upper surface of the belt 151 with the load sensors 153 arranged at four corners interposed therebetween.

The load sensor 153 is, for example, a load cell, and functions as a detection unit for detecting a load received from the foot of the trainee 900 standing on the riding plate 152. The load sensors 153 can detect the load received from the trainee 900 more quickly than when the load distribution sensor 154 described later is used to detect the load received from the trainee 900. The load sensors 153 are arranged at four corners of the riding plate 152 and support the riding plate 152. These four sensors may be collectively referred to as one load sensor 153.

The load distribution sensor 154 is composed of a plurality of sensors. The plurality of sensors are arranged in a matrix on the riding plate 152. The load distribution sensor 154 can detect the distribution of the surface pressure received from the trainee 900's feet using the plurality of sensors. Thus, the load distribution sensor 154 can identify the positions (standing position) of the trainee 900's feet in the standing state.

The handrail 170 is provided so as to be positioned, for example, on the side of the trainee 900 so that it can be graped when he/she is about to lose his/her balance or when he/she feels uneasy.

The control unit 160 calculates a reference position BP of the trainee 900 based on the positions of the trainee 900's feet detected by the load distribution sensor 154 before the training is started. As an example, the reference position BP is located at the center of a line segment connecting a position forward of the right foot sole equal to 40% of the length of the right foot sole starting from the rear end (heel part) of the right foot sole to a position forward of the left foot sole equal to 40% of the length of the left foot sole starting from the rear end (heel part) of the left foot sole.

The control unit 160 calculates the center of gravity position CP0 of the trainee 900 in a stationary standing state based on the load received from the trainee 900's feet detected by the load sensors 153 before the training is started. Note that the reference position BP and the center of gravity position CP0 may be at the same position consequently.

After that, the control unit 160 periodically calculates the center of gravity position CP1 of the trainee 900 based on the load received from the the trainee 900's feet detected by the load sensors 153 during the balance training.

Then, the control unit 160 rotates the pulley 155 at a speed, a direction, and an amount corresponding to a change of the center of gravity position with respect to the reference position BP (which is a mobile vector from the center of gravity position CP0 to the center of gravity position CP1) to thereby rotate the ring-shaped belt 151. The trainee 900 standing on the belt 151 also moves with the rotation of the belt 151.

Here, when the load distribution sensor 154 detects that the positions of the trainee 900's feet have changed, the control unit 160 recalculates the reference position BP based on the changed positions of the trainee 900's feet (i.e., the reference position BP is updated). At this time, the control unit 160 recalculates the center of gravity position CP0 in the stationary standing state of the trainee 900 after the standing position is changed. After that, the control unit 160 periodically calculates the center of gravity position CP1 of the trainee 900 during the balance training as usual.

The control unit 160 rotates the pulley 155 based on the change of the center of gravity position with respect to the updated reference position BP (i.e., the mobile vector from the updated center of gravity position CP0 to the center of gravity position CP1), thereby rotating the ring-shaped belt 151.

Thus, in the balance training system 100, even when the positions of the feet of the trainee 900 who is riding on the treadmill 150 are changed, the reference position BP is reset based on the changed standing position of the trainee 900. This enables control of the movement (rotation) of the belt 151 accurately according to the change of the center of gravity position with respect to the reset reference position BP, so that the trainee 900 can perform effective training.

The balance training system 100 uses the load sensors 153 to detect the load received from the trainee 900, so that the center of gravity position of the trainee 900 can be calculated more quickly than when the load distribution sensor 154 is used. Therefore, the balance training system 100 can more accurately control the movement of the belt 151.

Next, an operation of the balance training system 100 will be described with reference to FIGS. 3 and 4.

Figure 3:
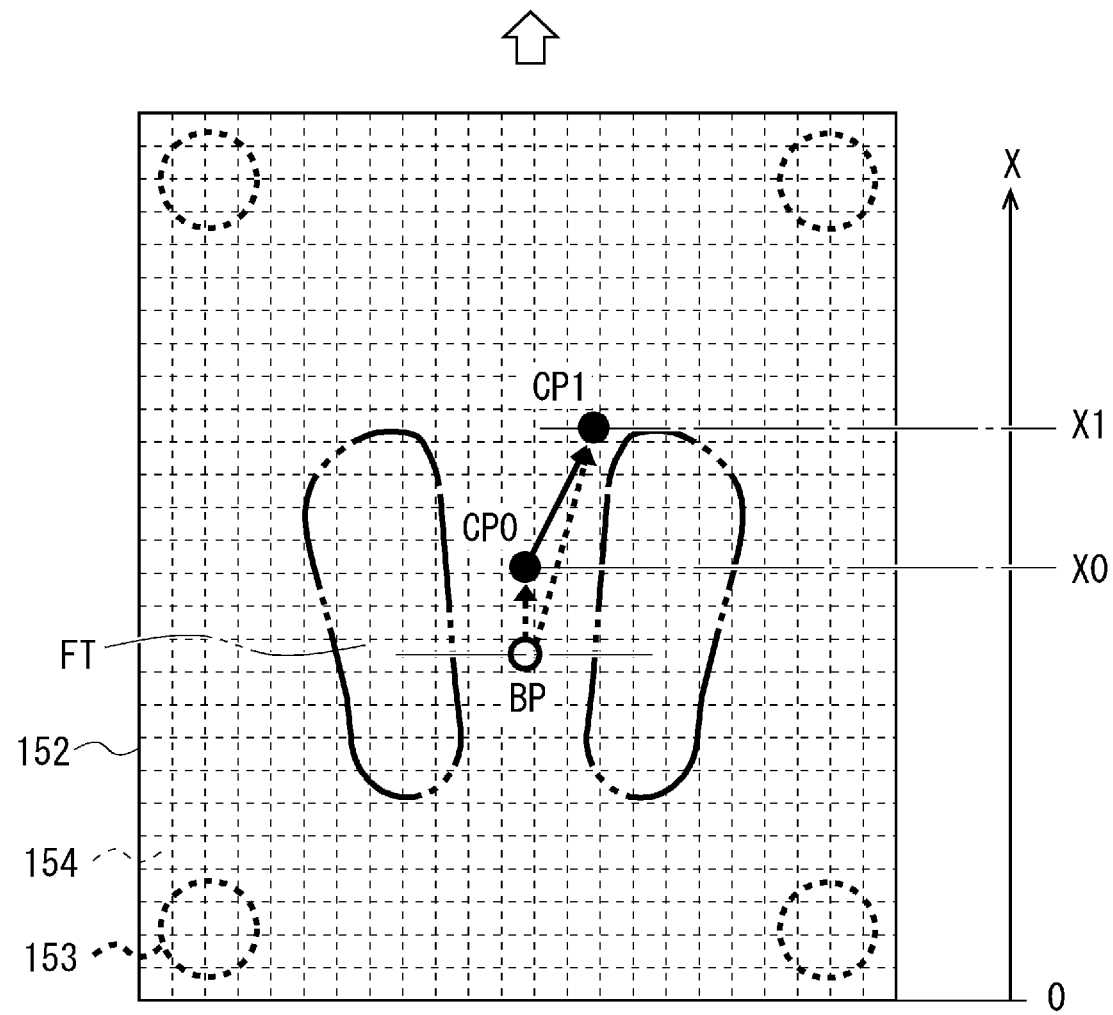
FIG. 3 is a diagram for explaining an operation of the balance training system shown in FIG. 1.
Figure 4:
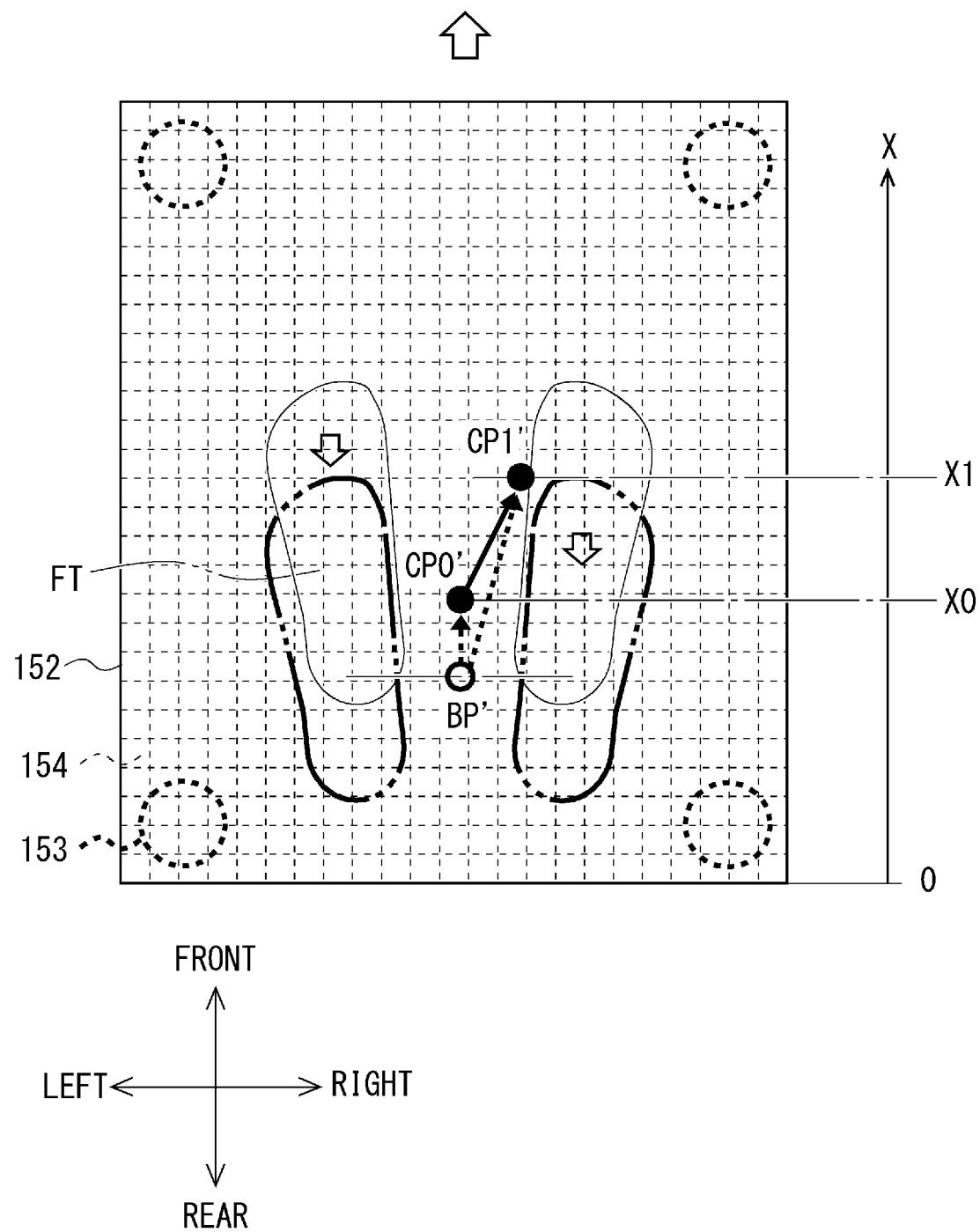
FIG. 4 is a diagram for explaining an operation of the balance training system shown in FIG. 1.

FIGS. 3 and 4 are diagrams for explaining the operation of the balance training system 100. FIG. 3 shows an example in which the standing position of the trainee 900 does not change. FIG. 4 shows an example in which the standing position of the trainee 900 is changed during training.

First, an example in which the standing position of the trainee 900 does not change will be described with reference to FIG. 3.

Before the training is started, the trainee 900 brings his/her sole to a specified position in a central part of the belt 151 and thus his/her state becomes a stationary standing state. When the training is started, the trainee 900 performs training to maintain his/her balance by attempting to move his/her center of gravity without moving the sole from the the position where the sole is brought into contact with the belt 151.

The control unit 160 calculates the reference position BP and the center of gravity position CP0 of the trainee 900 in the stationary standing state before the training is started. Specifically, the control unit 160 calculates the reference position BP of the trainee 900 based on the positions of the left and right feet FT of the trainee 900 detected by the load distribution sensor 154, and calculates the initial center of gravity position CP0 of the trainee 900 based on the loads received by the riding plate 152 from the left and right feet FT of the trainee 900 detected by the load sensors 153.

When the training is started, the control unit 160 periodically calculates the center of gravity position CP1 of the trainee 900 during the balance training from a result of the detection by the load sensors 153. In the example of FIG. 3, during the balance training, the trainee 900 inclines his/her weight to diagonally forward right more than when he/she is in the stationary standing state. Thus, the center of gravity position CP1 is positioned diagonally forward right of the initial center of gravity position CP0.

The control unit 160 rotates the belt 151 in accordance with the mobile vector (the solid arrow in FIG. 3) from the relative position of the center of gravity CP0 with respect to the reference position BP to the relative position of the center of gravity CP1 with respect to the reference position BP. The trainee 900 standing on the belt 151 also moves with the rotation of the belt 151. In this example, the belt 151 can rotate only in the front-rear direction.

The X-axis shown in FIG. 3 indicates the position of the center of gravity in the front-rear direction when the rear end of the rectangular riding plate 152 is defined as a starting point. In the example of FIG. 3, the initial position of the center of gravity CP0 is the position X0, and the position of the center of gravity CP1 is the position X1. The control unit 160 rotates the belt 151 forward or backward according to the difference between the positions X1 and X0. In the example of FIG. 3, the control unit 160 rotates the belt 151 forward according to the difference between the positions X1 and X0. Thus, the trainee 900 standing on the belt 151 also moves forward.

Next, an example in which the standing position of the trainee 900 changes during the training will be described with reference to FIG. 4.

The control unit 160 calculates the reference position BP and the center of gravity position CP0 of the trainee 900 in the stationary standing state (not shown in FIG. 4). The method of calculating the reference position BP and the center of gravity position CP0 is the same as that in the case of FIG. 3, and the description thereof is omitted accordingly.

When the training is started, the control unit 160 periodically calculates the center of gravity position CP1 of the trainee 900 during the balance training from a result of the detection by the load sensors 153 (not shown in FIG. 4). Then, the control unit 160 rotates the belt 151 in accordance with the mobile vector from the relative position of the center of gravity CP0 with respect to the reference position BP to the relative position of the center of gravity CP1 with respect to the reference position BP.

Here, when the load distribution sensor 154 detects that the positions of the trainee 900's feet have changed, the control unit 160 recalculates the reference position BP (the reference position BP' in FIG. 4) based on the changed positions of the trainee 900's feet FT. At this time, the control unit 160 recalculates the center of gravity position CP0 (center of gravity position CP0' in FIG. 4) of the trainee 900 in the stationary standing state. That is, when the positions FT of the the trainee 900's feet change, the control unit 160 resets the center of gravity position CP0 as a reference based on the changed standing position of the trainee 900.

After that, the control unit 160 periodically calculates the center of gravity position CP1 (the center of gravity position CP1' in FIG. 4) of the trainee 900 during the balance training as usual from a result of the detection by the load sensors 153. In the example of FIG. 4, during the balance training, the trainee 900 inclines his/her weight to diagonally forward right more than when he/she is in the stationary standing state after the standing position is changed. Thus, the center of gravity position CP1 is positioned diagonally forward right of the center of gravity position CP0.

Then, the control unit 160 rotates the belt 151 in accordance with the mobile vector from the relative position of the center of gravity CP0 with respect to the reference position BP to the relative position of the center of gravity CP1 with respect to the reference position BP.

As described so far, in the balance training system 100, even when the positions of the feet of the trainee 900 who is riding on the treadmill 150 are changed, the reference position BP is reset based on the changed standing position of the trainee 900. This enables control of the movement (rotation) of the belt 151 accurately according to the change of the center of gravity position with respect to the reset reference position BP, so that the trainee 900 can perform effective training.

Second Embodiment

Figure 5:
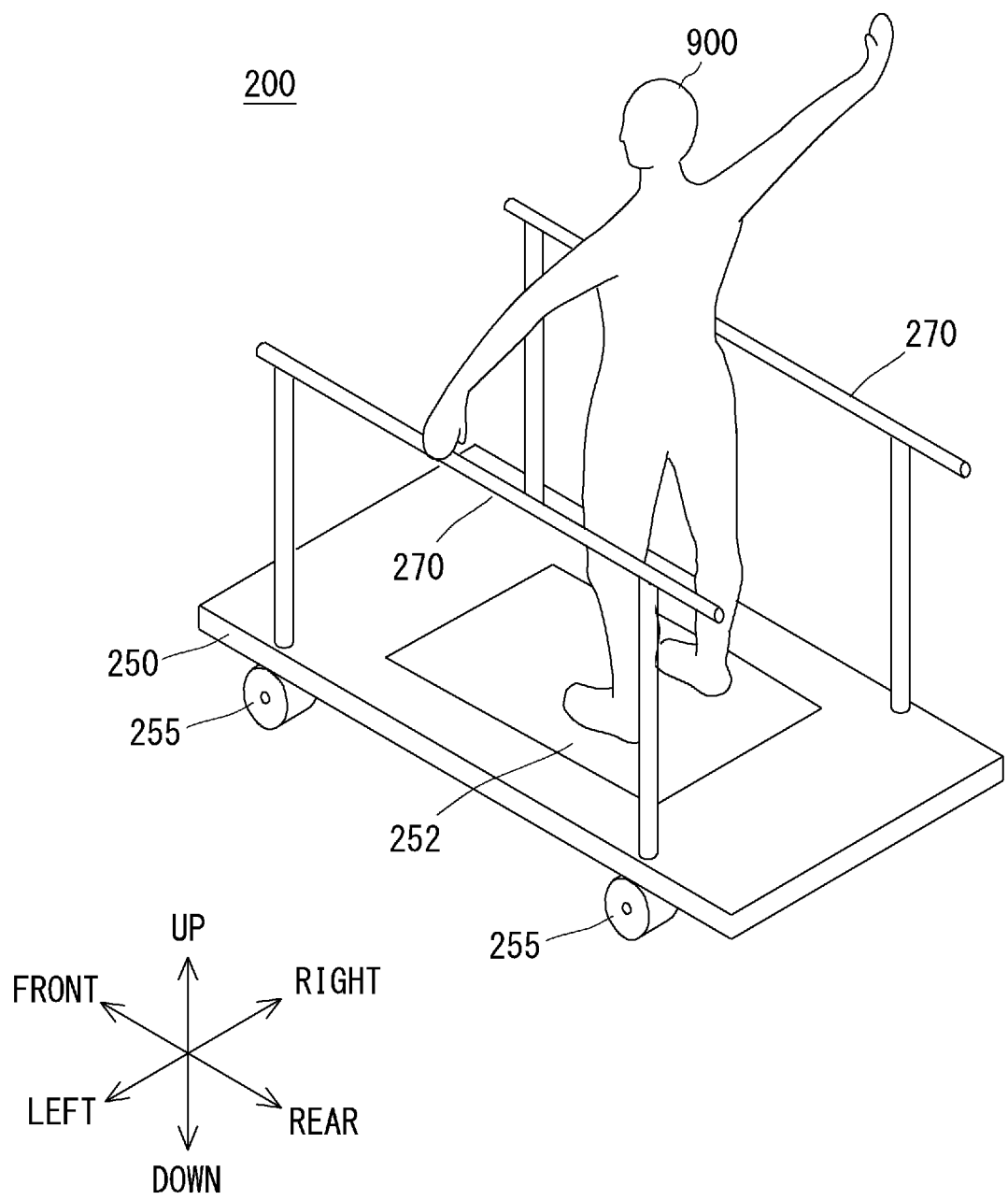
FIG. 5 is an overview perspective view of a balance training system according to a second embodiment.
Figure 6:
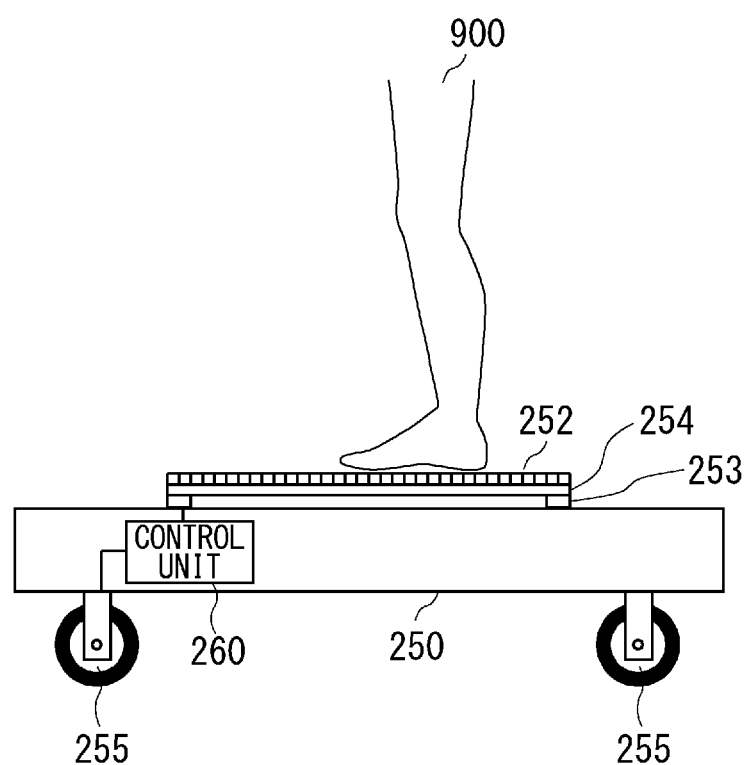
FIG. 6 is an overview side view of a part of the balance training system shown in FIG. 5.

FIG. 5 is an overview perspective view (view from diagonally backward left) of a balance training system 200 according to a second embodiment. FIG. 6 is an overview side view (view from the left) of a part of the balance training system 200. The balance training system 200 may also be referred to as a balance training device.

The balance training system 200 includes a moving carriage (mobile body) 250, a riding plate 252, load sensors 253, a load distribution sensor 254, a control unit 260, and a handrail 270. The riding plate 252, the load sensors 253, the load distribution sensor 254, the control unit 260, and the handrail 270 correspond to the riding plate 152, the load sensors 153, the the load distribution sensor 154, the control unit 160, and the handrail 170, respectively. Note that, in the following description, the up-down direction, the right-left direction, and the front-rear direction are directions based on the orientation of the trainee 900.

The moving carriage 250 is configured to be movable in the front-rear direction on a moving surface of a floor surface or the like of a rehabilitation facility as the moving surface. The riding plate 252, the load sensors 253, and the load distribution sensor 254 are disposed on the moving carriage 250.

The handrail 270 is provided so as to be positioned, for example, on the side of the trainee 900 so that it can be graped when he/she is about to lose his/her balance or when he/she feels uneasy.

The control unit 260 calculates the reference position BP and the center of gravity position CP0 of the trainee 900 in a stationary standing state before starting training. When the training is started, the control unit 260 periodically calculates the center of gravity position CP1 of the trainee 900. Then, the control unit 260 rotates wheels 255 at a speed, a direction, and an amount corresponding to a change of the center of gravity position with respect to the reference position BP (which is the mobile vector from the center of gravity position CP0 to the center of gravity position CP1) to thereby move the moving carriage 250. The trainee 900 standing on the moving carriage 250 also moves with the movement of the moving carriage 250.

When the load distribution sensor 254 detects that the positions of the the trainee 900's feet have changed, the control unit 260 recalculates the reference position BP based on the changed positions of the trainee 900's feet. At this time, the control unit 260 recalculates the center of gravity position CP0 of the trainee 900 in the stationary standing state. That is, when the positions FT of the the trainee 900's feet changes, the control unit 260 resets the center of gravity position CP0 as a reference based on the changed standing position of the trainee 900. After that, the control unit 260 periodically calculates the center of gravity position CP1 of the trainee 900 during the balance training as usual. The control unit 260 moves the wheels 255 based on the change of the center of gravity position with respect to the updated reference position BP (which is the mobile vector from the updated center of gravity position CP0 to the center of gravity position CP1), thereby rotating the ring-shaped belt 151.

Thus, the balance training system 200 can also exhibit effects equivalent to those of the balance training system 100.

The present disclosure is not limited to the first and second embodiments described above, and may be modified as appropriate without departing from the spirit of the disclosure.

In the first embodiment, a case in which the control unit 160 rotates the belt 151 in the front-rear direction in accordance with the mobile vector from the center of gravity CP0 to the center of gravity CP1 has been described as an example. However, the present disclosure is not limited to this. If the belt 151 is configured to be rotatable not only in the front-rear direction but also in the right-left direction, the control unit 160 can rotate the belt 151 in the front-rear and right-left directions in accordance with the mobile vector from the center of gravity CP0 to the center of gravity CP1.

Likewise, in the second embodiment, an example in which the control unit 260 moves the moving carriage 250 in the front-rear direction in accordance with the mobile vector from the center of gravity CP0 to the center of gravity CP1 has been explained. However, the present disclosure is not limited to this. If the moving carriage 250 is configured to be movable not only in the front-rear direction but also in the right-left direction, the control unit 260 can move the moving carriage 250 in the front-rear and right-left directions in accordance with the mobile vector from the center of gravity CP0 to the center of gravity CP1.

In the first embodiment, an example in which the control unit 160 is included in the treadmill 150 has been explained. However, the present disclosure is not limited to this. The control unit 160 may be provided outside the treadmill 150, or may be configured to remotely control the treadmill 150. Similarly, in second embodiment, although an in which the control unit 260 is included in the moving carriage 250 has been explained, the present disclosure is not limited to this. The control unit 260 may be provided outside the moving carriage 250, or may be configured to remotely control the moving carriage 250.

Further, although the present disclosure has been explained in the above embodiments as a hardware configuration, the present disclosure is not limited to this. The present disclosure can be realized by causing a CPU (Central Processing Unit) to execute a computer program for controlling a balance training system.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A balance training system comprising:
   a riding plate including a mounting surface for supporting a sole of a trainee in a standing state;
   a load distribution sensor including a plurality of sensors arranged in a matrix on the riding plate and configured to detect positions of feet of the trainee riding on the riding plate;
   a load sensor configured to detect a load received by the riding plate from the trainee;
   a mobile body, the riding plate, the load distribution sensor, and the load sensor being disposed on the mobile body; and
   a control unit configured to calculate a reference position based on the positions of the feet of the trainee detected by the load distribution sensor, then calculate a center of gravity position of the trainee based on the load detected by the load sensor, and control a movement of the mobile body based on a change of the center of gravity position with respect to the reference position, wherein
   the control unit is configured to update the reference position based on changed positions of the feet of the trainee when a change of a position of at least one of the feet of the trainee is detected by the load distribution sensor.

2. The balance training system according to claim 1, wherein
   the control unit is configured to control a moving direction and a moving amount of the mobile body based on a changing direction and a changing amount of the center of gravity position of the trainee with respect to the reference position.

3. The balance training system according to claim 1, wherein
   the mobile body is a belt of a treadmill, and the riding plate, the load distribution sensor, and the load sensor are disposed on the belt of the treadmill.

4. The balance training system according to claim 1, wherein
   the mobile body is a moving carriage, and
   the riding plate, the load distribution sensor, and the load sensor are disposed on the moving carriage.

5. A method of controlling a balance training system comprising:
   detecting, using a load distribution sensor composed of a plurality of sensors arranged in a matrix on a riding plate, positions of feet of a trainee riding on the riding plate, the riding plate including a mounting surface for supporting a sole of the trainee in a standing state;
   detecting, using a load sensor, a load received by the riding plate from the trainee; and
   calculating a reference position based on the positions of the feet of the trainee detected by the load distribution sensor, then calculating a center of gravity position of the trainee based on the load detected by the load sensor, and controlling a movement of a mobile body, on which the riding plate, the load distribution sensor, and the load sensor are disposed, based on a change of the center of gravity position with respect to the reference position, wherein
   in the controlling of the movement of the mobile body, the reference position is updated based on changed positions of the feet of the trainee when a change of a position of at least one of the feet of the feet of the trainee is detected by the load distribution sensor.

6. A non-transitory computer readable medium storing a control program, the control program causing a computer to execute:
   a process of detecting, using a load distribution sensor composed of a plurality of sensors arranged in a matrix on a riding plate, positions of feet of a trainee riding on the riding plate, the riding plate including a mounting surface for supporting a sole of the trainee in a standing state;
   a process of detecting, using a load sensor, a load received by the riding plate from the trainee; and
   a process of calculating a reference position based on the positions of the feet of the trainee detected by the load distribution sensor, then calculating a center of gravity position of the trainee based on the load detected by the load sensor, and controlling a movement of a mobile body, on which the riding plate, the load distribution sensor, and the load sensor are disposed, based on a change of the center of gravity position with respect to the reference position, wherein
   in process of the controlling the movement of the mobile body, the reference position is updated based on changed positions of the feet of the trainee when a change of a position of at least one of the feet of the trainee is detected by the load distribution sensor.

* * * * *